(12) United States Patent
Cronin et al.

(10) Patent No.: US 10,993,830 B2
(45) Date of Patent: May 4, 2021

(54) SCALP COOLING APPARATUS, METHOD, AND SYSTEM

(71) Applicant: Dignitana AB, Lund (SE)

(72) Inventors: William Cronin, Dallas, TX (US); Jim McKinney, Dallas, TX (US); Rickard Norenstam, Lund (SE); Robert J. Lang, Alamo, CA (US)

(73) Assignee: Dignitana AB, Lund (SE)

( * ) Notice: Subject to any disclaimer, the term of this patent is extended or adjusted under 35 U.S.C. 154(b) by 0 days.

(21) Appl. No.: 16/679,722

(22) Filed: Nov. 11, 2019

(65) Prior Publication Data

US 2020/0146878 A1     May 14, 2020

Related U.S. Application Data

(60) Provisional application No. 62/758,080, filed on Nov. 9, 2018.

(51) Int. Cl.
*A61F 7/00* (2006.01)
*A61B 5/107* (2006.01)
(Continued)

(52) U.S. Cl.
CPC .......... *A61F 7/0085* (2013.01); *A42B 1/008* (2013.01); *A61B 5/1079* (2013.01); *G06F 30/00* (2020.01);
(Continued)

(58) Field of Classification Search
CPC combination set(s) only.
See application file for complete search history.

(56) References Cited

U.S. PATENT DOCUMENTS

| 1,523,941 A | 1/1925 | Fliegel |
| 1,862,161 A | 6/1932 | Reynolds |

(Continued)

FOREIGN PATENT DOCUMENTS

| CN | 201029963 Y | 3/2008 |
| CN | 205849752 U | 1/2017 |

(Continued)

*Primary Examiner* — Joseph A Stoklosa
*Assistant Examiner* — Adam J Avigan
(74) *Attorney, Agent, or Firm* — Vincent J. Allen; J. Andrew Reed; Carstens & Cahoon, LLP

(57) ABSTRACT

A scalp cooling apparatus, method, and system that may include an inner scalp cap, an intermediate scalp covering, and an outer scalp cap. The inner scalp cap may be fluidly coupled to a cooling device, that would allow a cooling fluid to traverse the fluid chambers within a set of sections of the inner scalp cap. The inner scalp covering can be constructed of a thermally conductive material. The intermediate scalp covering can be constructed of a thermally neutral material. The outer scalp covering can be constructed of a thermally resistant material. The outer scalp covering may have a first securing mechanism, and a second securing mechanism, that allow the outer scalp covering to be dynamically adjusted and secured against a patient's scalp via the first securing mechanism and the second securing mechanism. The inner scalp cap may be created from a scan of a patient's head, that can then be utilized as an interpolated parametric model may be utilized to generate an output file.

20 Claims, 11 Drawing Sheets

(51) Int. Cl.
 *A42B 1/00* (2021.01)
 *G06F 30/00* (2020.01)
 *A42B 1/008* (2021.01)
(52) U.S. Cl.
 CPC ........... *A61F 2007/0008* (2013.01); *A61F 2007/0056* (2013.01)

(56) References Cited

U.S. PATENT DOCUMENTS

| | | | |
|---|---|---|---|
| 2,503,432 | A | 4/1950 | Bowers |
| 4,382,446 | A | 5/1983 | Truelock et al. |
| 4,552,149 | A * | 11/1985 | Tatsuki ............... A61F 7/10 607/110 |
| 4,566,455 | A | 1/1986 | Kramer |
| 4,599,749 | A | 7/1986 | Childs et al. |
| 4,765,338 | A | 8/1988 | Turner et al. |
| 5,342,411 | A | 8/1994 | Maxted et al. |
| 5,493,735 | A | 2/1996 | Rice |
| 5,956,759 | A | 9/1999 | Benedict |
| 6,156,059 | A | 12/2000 | Olofsson |
| 6,312,453 | B1 | 11/2001 | Stefanile et al. |
| 6,324,700 | B1 | 12/2001 | McDougall |
| 6,738,986 | B1 | 5/2004 | Martin |
| 7,493,168 | B2 | 2/2009 | Rezai |
| 7,722,656 | B1 | 5/2010 | Segal |
| 8,117,679 | B2 | 2/2012 | Pierce |
| 8,529,613 | B2 | 9/2013 | Radziunas et al. |
| 9,101,463 | B2 | 8/2015 | Stormby |
| 9,610,185 | B2 | 4/2017 | Capra et al. |
| 9,743,701 | B2 | 8/2017 | Javorek et al. |
| 9,894,953 | B2 | 2/2018 | Szalkowski et al. |
| 2005/0096714 | A1 | 5/2005 | Freedman, Jr. et al. |
| 2009/0254159 | A1 | 10/2009 | Stormby |
| 2010/0037908 | A1 | 2/2010 | Hatcher et al. |
| 2010/0186436 | A1 | 7/2010 | Stormby |
| 2010/0324635 | A1 | 12/2010 | Kreck |
| 2011/0099690 | A1 | 5/2011 | Higgins et al. |
| 2011/0283440 | A1 | 11/2011 | Higgins et al. |
| 2014/0046410 | A1 | 2/2014 | Wyatt |
| 2014/0221889 | A1 | 8/2014 | Burns et al. |
| 2014/0343599 | A1 | 11/2014 | Smith et al. |
| 2015/0190262 | A1 | 7/2015 | Capra et al. |
| 2016/0174648 | A1 | 6/2016 | Garneau et al. |
| 2016/0198803 | A1 | 7/2016 | Soderberg et al. |
| 2016/0317348 | A1 | 11/2016 | Banker |
| 2016/0354223 | A1 | 12/2016 | Burns et al. |
| 2016/0374886 | A1 | 12/2016 | Wyatt et al. |
| 2017/0006951 | A1 | 1/2017 | Venturini et al. |
| 2017/0239083 | A1 * | 8/2017 | Unver ................ A61F 7/10 |
| 2018/0055721 | A1 | 3/2018 | Quisenberry et al. |
| 2018/0303662 | A1 | 10/2018 | Berg |

FOREIGN PATENT DOCUMENTS

| | | |
|---|---|---|
| CN | 206167166 U | 5/2017 |
| EP | 0087815 A1 | 9/1983 |
| EP | 31473891 A2 | 3/2017 |
| JP | 2001502207 A | 2/2001 |
| WO | 2008070198 A2 | 6/2008 |
| WO | 2016046535 A1 | 3/2016 |

* cited by examiner

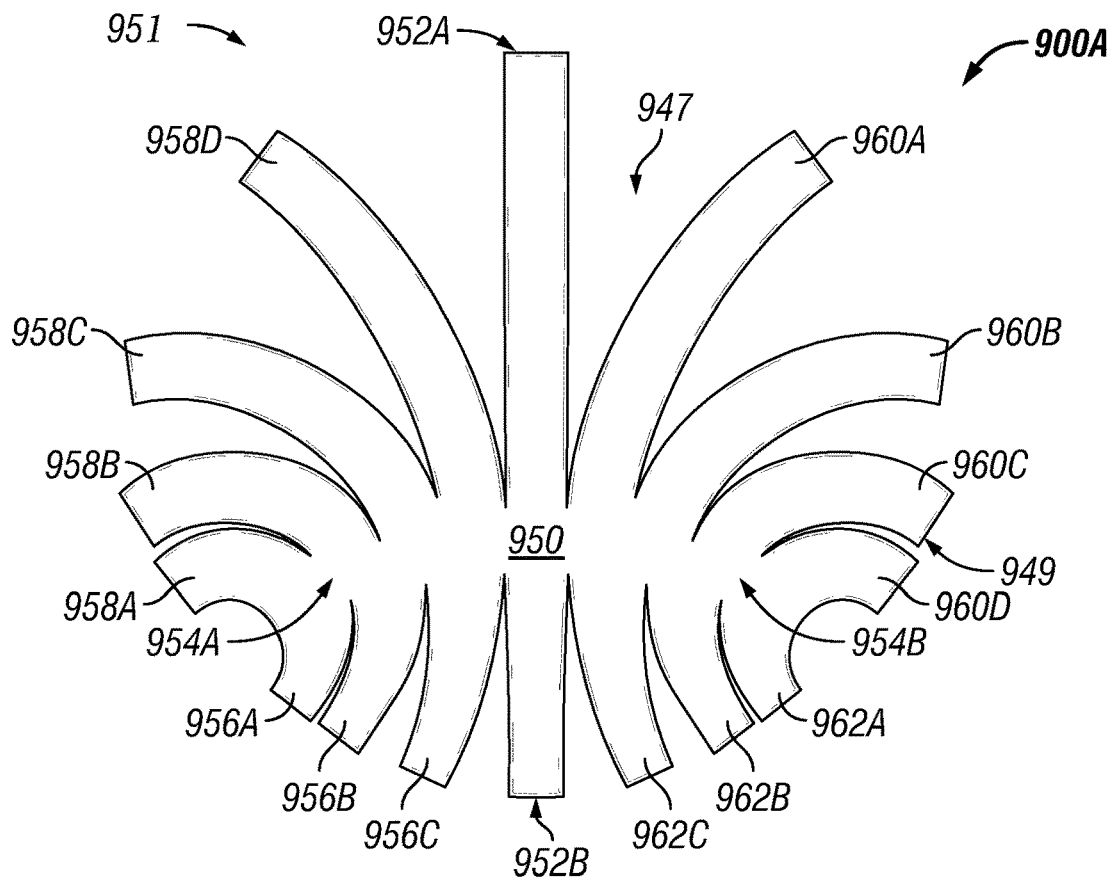
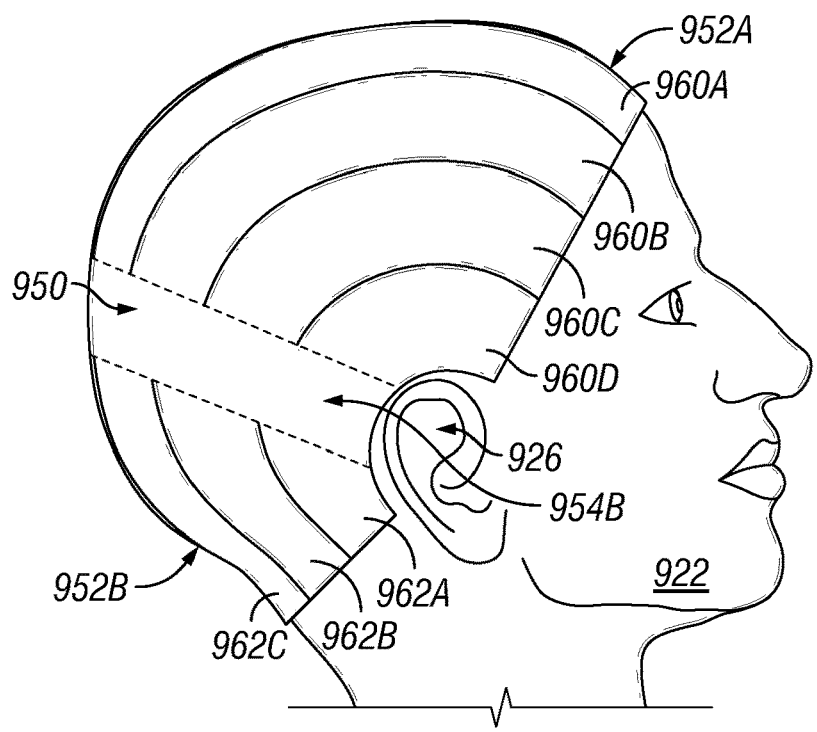
FIG. 9A
FIG. 9B

SCALP COOLING APPARATUS, METHOD, AND SYSTEM

CROSS-REFERENCE TO RELATED APPLICATIONS

This application claims the benefit of U.S. Provisional Application No. 62/758,080, filed Nov. 9, 2018, of which is incorporated herein by reference in its entirety.

BACKGROUND

Technical Field

The present disclosure relates to biological cooling. More particularly, and not by way of limitation, the present disclosure is directed to an apparatus, system, and method for cooling of a scalp.

Description of Related Art

During chemotherapy or other cancer treatments, a patient's hair will typically fall out due to the various treatments and chemicals utilized to battle the cancer cells. However, it has also been discovered that when the scalp is cooled during these treatments the amount of hair loss is reduced. The reduced temperatures result in a reduced blood flow to the scalp area so that less chemotherapy reaches the hair cells.

Dignitana AB has been a leader in the development of hair loss treatments for cancer patients, and has filed a number of patent applications covering head cooling devices including U.S. Pat. Nos. 9,421,125, 9,101,463, and PCT/EP2008/051890; a scalp cooling apparatus U.S. Pat. No. 6,156,059; and methods and devices for controlling the temperature of local regions of a patient's body U.S. application Ser. No. 12/086,060, and PCT/SE2006/001383. These patents and applications are incorporated herein by reference.

Current systems allow for a one size fits all silicon cap, thermal cap, and an outer cap to be utilized, that can result in unreliable fit and/or the possibility of infections or other viruses. It would be advantageous to have an apparatus, system, and method for cooling of a scalp that overcomes the disadvantages of the prior art. The present disclosure provides such a system and method.

BRIEF SUMMARY

The present disclosure is directed to the cooling of a human scalp. Thus, in one aspect, the present disclosure is directed to an apparatus for a scalp covering that may include a linking section having a first end and a second end. A forward central section is coupled perpendicularly to the linking section at a first end. A rearward central section is coupled perpendicularly to the linking section at a first end. A first set of forward radial sections is coupled to the linking section, a second set of forward radial sections is coupled to the linking section, a first set of rearward radial sections is coupled to the linking section, and a second set of rearward radial sections is coupled to the linking section.

In another aspect, the present disclosure is directed to a system for scalp covering including an inner scalp covering, an intermediate scalp covering, and an outer scalp covering. The inner scalp covering can be constructed of a thermally conductive material. The intermediate scalp covering can be constructed of a thermally neutral material. The outer scalp covering can be constructed of a thermally resistant material. The inner scalp covering may be coupled via fluid channels to a cooling device, and the cooling device fluidly coupled to a set of sections of the inner scalp covering for interfacing with a patient's scalp. The outer scalp covering may include a first securing mechanism, and a second securing mechanism, that allow the outer scalp covering to be dynamically adjusted and secured against a patient's scalp via the first securing mechanism and the second securing mechanism.

In yet another aspect, the present disclosure is directed to a method of manufacture for a scalp covering including scanning a patient's scalp to generate a scan data set, importing the scan data set, creating a parametric model from the scan data set, interpolating the parametric model, remapping the parametric model, generating a design file from the remapped parametric model, and outputting the design file. The scanning may be completed utilizing a three-dimensional scanner. The creation of the parametric model can also include calculating a centroid point of the patient's ear, calculating an azimuthal angle of the patient's forehead hairline, and calculating an azimuthal angle of the patient's nape hairline. Interpolation can include calculating a head radius, and calculating a head surface. The generated design file can include calculations for the width of a section of the scalp covering, the radial angles for a section of the scalp covering, and calculating the number of sections for the scalp covering.

In yet another aspect, the present disclosure is directed to a method of use for a scalp covering system including, placing an inner scalp covering over a patient's scalp, covering the inner scalp covering with an intermediate scalp covering, interfacing an outer scalp covering with the intermediate scalp covering and the inner scalp covering, and securing the outer scalp covering to the patient's scalp utilizing at least two securing mechanisms coupled to the outer scalp covering. The inner scalp may be fluidly coupled to a cooling device via channels in the inner scalp covering. The tightening of the inner scalp covering can also tighten the intermediate scalp covering via hook and loop straps of a connecting strap with a first side and a second side of the outer scalp covering. The tightening can also be competed through a buckle at a first end of the connecting strap, or a second end of the connecting strap. The outer scalp covering may have at least two securing mechanisms to tighten a securing cable coupled to each of the at least two securing mechanisms or release the two securing mechanisms.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

FIG. 9A is an illustration of a design file output from a parametric processing.

FIG. 9B is an illustration of a design file output from a parametric processing, placed on the head of a patient.

DETAILED DESCRIPTION

Figure 1:
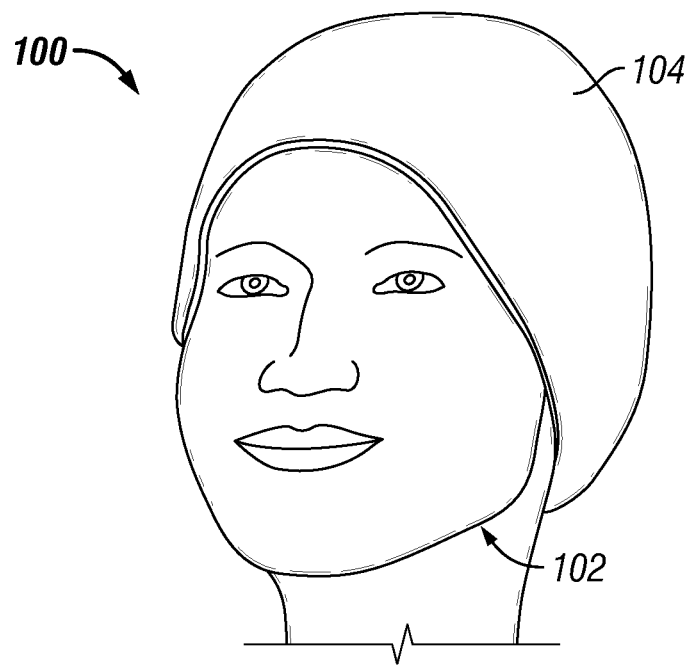
FIG. 1 is an illustration of a patient with a scalp cap that can be utilized with a cooling system.

FIG. 1 is an illustration of a patient 102 with a scalp cap 104 utilized with a cooling system. The scalp cap 104 can be a silicon or other material that is thermally conductive but is a single piece of material with no cuts or trimming lines. The scalp cap 104 would not allow for a complete fit due to the nature of the material not conforming with a patient's scalp. The shape of a patient's scalp can present issues when the scalp cap 104 is constructed based on a one size fits all model. To provide effective cooling the scalp cap 104 must maintain a maximum contact with the patient's scalp, which is impossible to do with generic or a fixed set of scalp cap 104 versions as each patient 102 has a unique scalp profile. Using prior designs, the temperature differences between the scalp and the scalp cap 104 could be more than eighteen (18) degrees centigrade.

Figure 2:
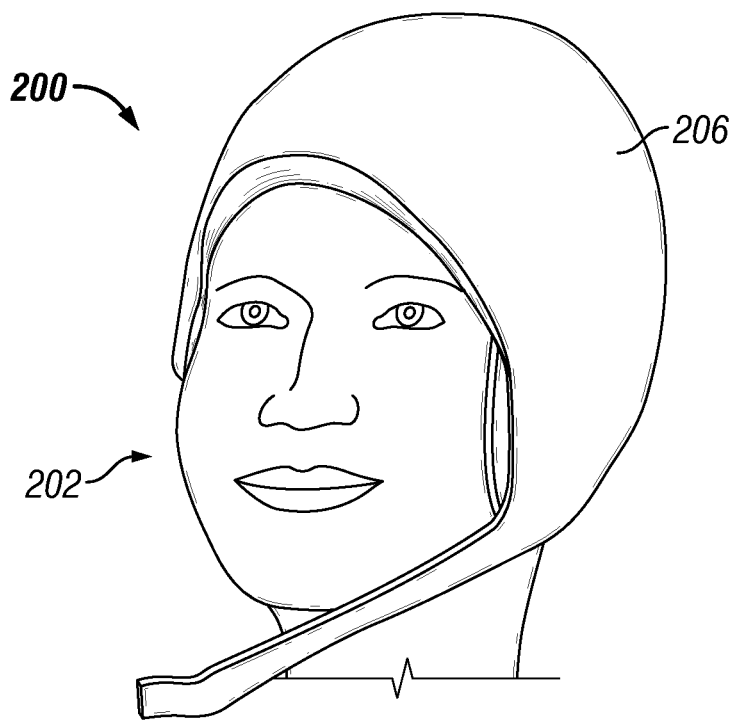
FIG. 2 is an illustration of a patient with a thermal cap that can be utilized with a cooling system.

FIG. 2 is an illustration of a patient 202 with a thermal cap 206 (or intermediate covering) to be utilized with a cooling system in at least one embodiment. The thermal cap 206 can be constructed of a thermally resistant or thermally reflective material such as cotton, ceramic, fiberglass, aluminized, silicone, silica, aramid, vermiculite, Z-block, acrylic, PTFE fabrics or infused fabrics. In at least one embodiment, the thermal cap 206 is made of cotton or other fabrics. A patient 202 can use the thermal cap 206 to prevent or reduce the amount of cooling lost to a room. For example, the thermal cap 206 may be utilized to increase the cooling effect of the cooling system and the scalp cap (not illustrated).

Figure 3A:
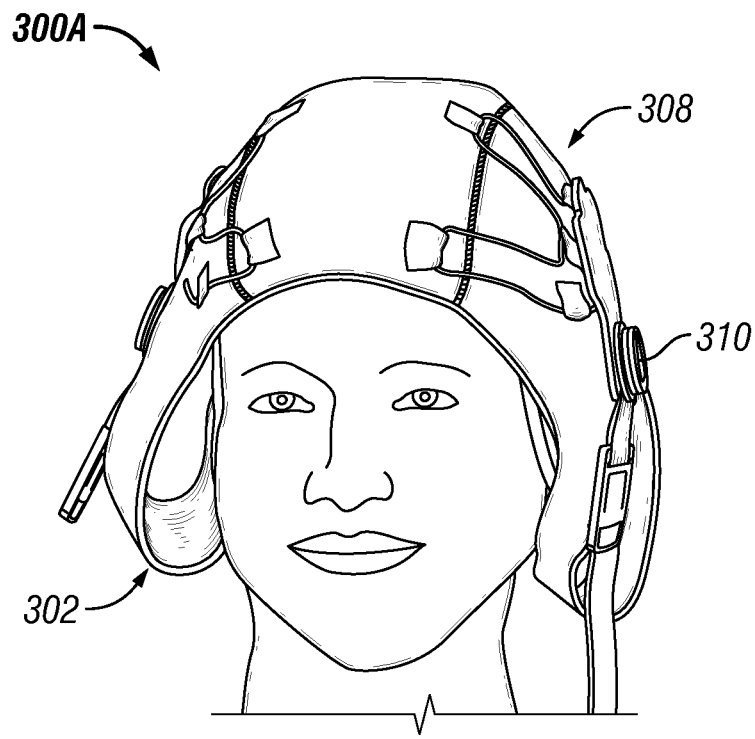
FIG. 3A is an illustration of the application of a securing cap to a patient for utilization with a cooling system.

FIG. 3A is an illustration of a patient 302 applying a securing cap 308 (or outer scalp covering) over a thermal cap (not illustrated) and/or scalp cap (not illustrated) for utilization with a cooling system. The securing cap 308 can include at least one securing mechanism 310 to increase pressure on the thermal cap (not illustrated) and/or the scalp cap (not illustrated). The at least one securing mechanism 310 can utilize a securing line 311 that can be tightened or released by the at least one securing mechanism. In some embodiments, the at least one securing mechanism 310 can be pressed in or clicked in, and rotated to tighten the securing line 311, and the at least one securing mechanism 310 can be pulled out or clicked out, to loosen the securing line 311. In other embodiments, the at least one securing mechanism 310 can be pulled out or clicked out, and rotated to tighten the securing line 311, and the at least one securing mechanism 310 can be pressed in or clicked in, to loosen the securing line 311. In at least one example, the securing cap 308 applies a pressure or securing pressure to the thermal cap (not illustrated) and also the scalp cap (not illustrated) to ensure that a scalp cap is as close to the scalp and/or maintains as much contact as possible to increase the amount of cooling for the patient's scalp and/or hairline.

Figure 3B:
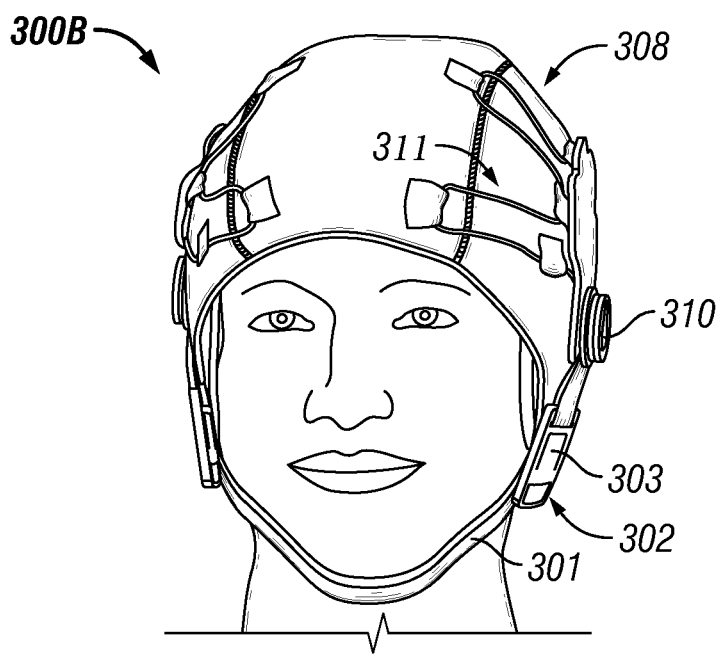
FIG. 3B is an illustration of the application of a securing cap for utilization with a cooling system.

FIG. 3B is an illustration of a patient 302 securing a securing cap 308 (or outer covering) over a thermal cap (not illustrated) and/or scalp cap (not illustrated) for utilization with a cooling system. In at least one version, the securing cap 308 can include a plurality of securing mechanisms 310. The securing mechanism(s) 310 can provide for an engagement or disengagement of the securing mechanism by the patient 302 that can include a tightening or loosening of the securing cap 308 against the thermal cap (not illustrated) and/or scalp cap (not illustrated). The at least one securing mechanism 310 can utilize a securing line 311 that can be tightened or released by the at least one securing mechanism. In some embodiments, the at least one securing mechanism 310 can have a knob that may be pressed in or clicked in, and rotated to tighten the securing line 311, and the at least one securing mechanism 310 can have a knob that may be pulled out or clicked out, to loosen the securing line 311. In other embodiments, the at least one securing mechanism 310 can have a knob that may be pulled out or clicked out, and rotated to tighten the securing line 311, and the at least one securing mechanism 310 can have a knob that may be pressed in or clicked in, to loosen the securing line 311. In some embodiments, the securing cap 308 can have a chin strap 301 or a connecting strap. The chin strap 301 may have a buckle 303 or other fastening mechanism such as, but not limited to, a button, clip, strap, or hook and loop fastening mechanisms.

Figure 4A:
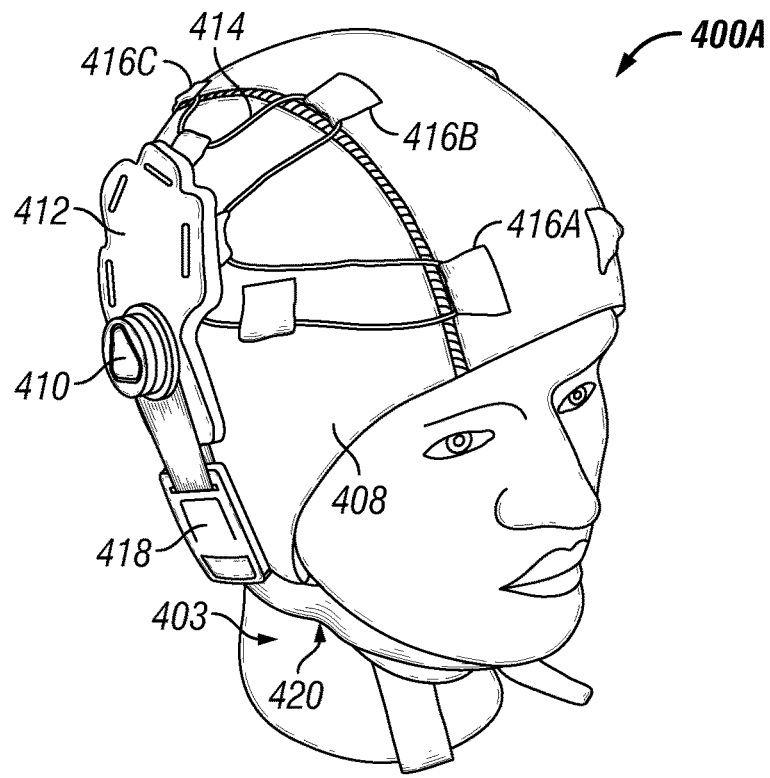
FIG. 4A is an illustration of a securing cap from a perspective view.
Figure 4B:
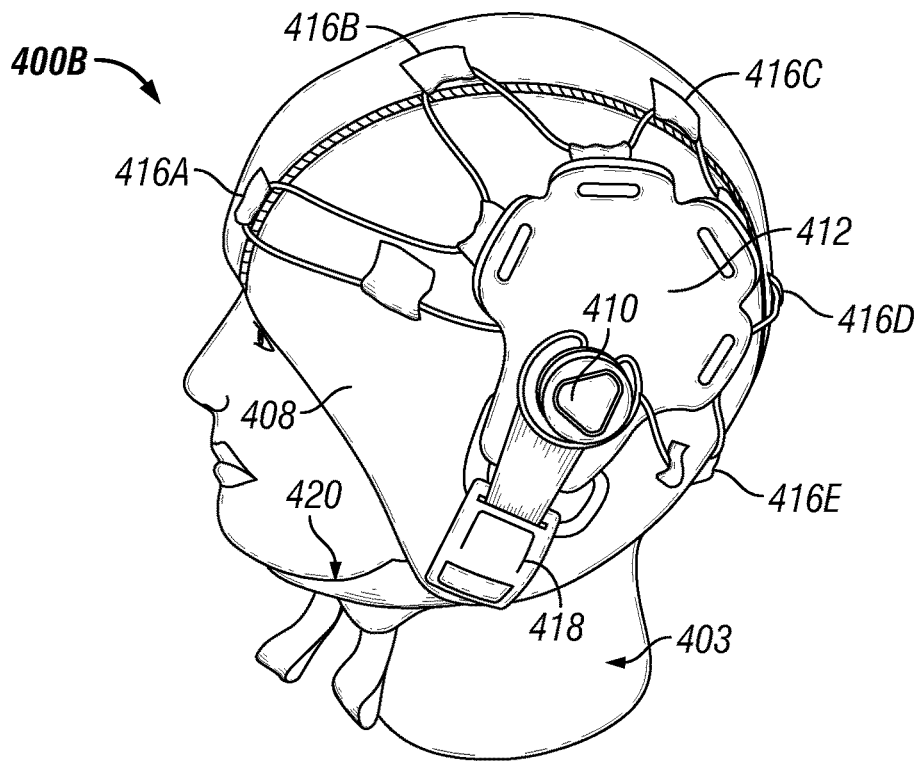
FIG. 4B is an illustration of a securing cap from a side view.

FIG. 4A is an illustration of a securing cap 408 from a perspective view. FIG. 4B is an illustration of a securing cap 408 from a side view. With respect to FIGS. 4A and 4B, a patient 402 can place the securing cap 408 on the head for use in securing and/or applying pressure to other caps beneath the securing cap 408. In at least one version the securing cap 408 can include at least two securing mechanism(s) 410. The at least two securing mechanism(s) 410 can be placed on a left side 403A and a right side 403A of a patient's head. The securing mechanism(s) 410 may be placed on a securing pad 412. The securing pad 412 can provide for a shifting of the securing mechanism(s) 410 as they are engaged or disengaged. The shifting accounts for variations in the head profile or size of a patient 402, allowing for the securing cap 408 and/or securing mechanism(s) 410 to provide a securing and comfortable fit. The securing mechanism(s) 410 in at least one example can be BOA® brand ratcheting mechanisms.

The securing mechanism(s) 410 can each have a securing line 414 passed through securing loop(s) 416A, 416B, 416C, 416D, and/or 416E (collectively 416). The securing loops(s) 416 can be coupled through thread, fastener such as, but not limited to hook and loop, glues, adhesives, or other similar or like methods of attachment and/or coupling to the securing cap 408. There may be additional or fewer securing loops(s) 416 based on the size and/or position of the securing mechanism(s) 410 in respect to the securing cap 408. In at least one version of the securing cap 408, a strap securer 418 and/or a chin strap 420 may also be utilized to increase the securability of the securing cap 408. The strap securing 418 and/or the chin strap 420 may allow for adjustability of the securing cap 408 under and/or around the chin or face of a patient.

Figure 5A:
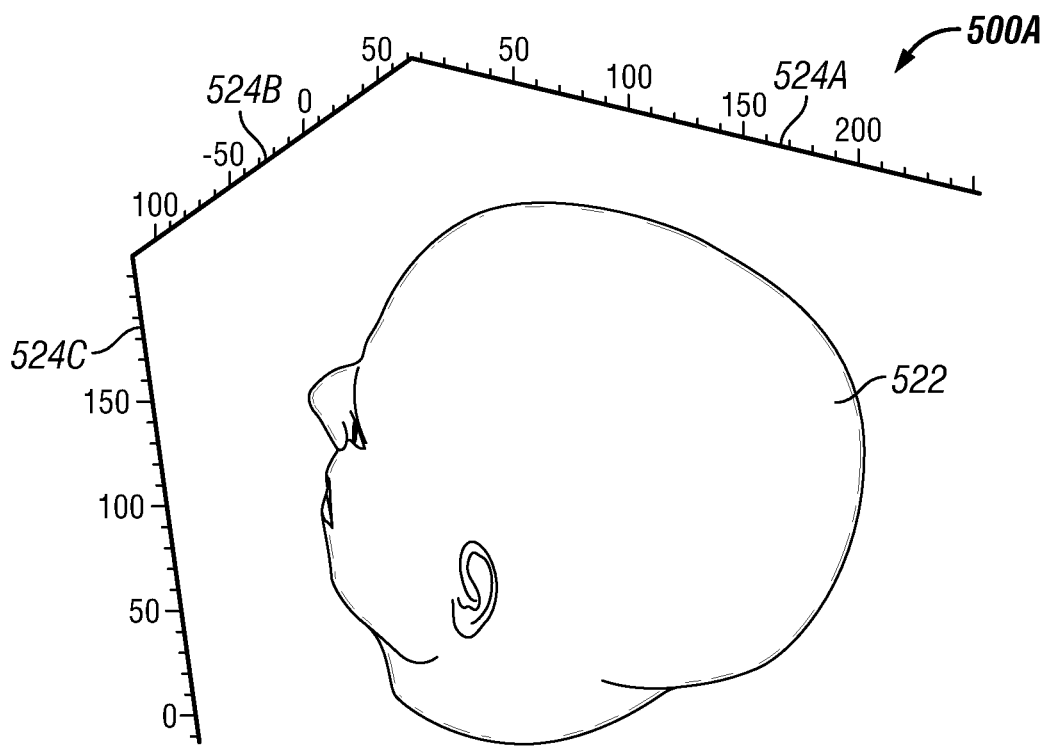
FIG. 5A is a perspective view illustration of a scanned head for a parametric processing.

FIG. 5A is a perspective view illustration of a scanned head 522 used for a parametric processing 500A. In at least one version of the parametric processing 500A, at least one axis is provided. The axis(s) 524A, 524B, and/or 524C provide a reference for the dimensions of a patient's head as scanned. The scanning can be performed utilizing a 3D scanner, images of the patient, X-rays, CAT scans, MIR imaging, or other methods of imaging and/or measuring.

Figure 5B:
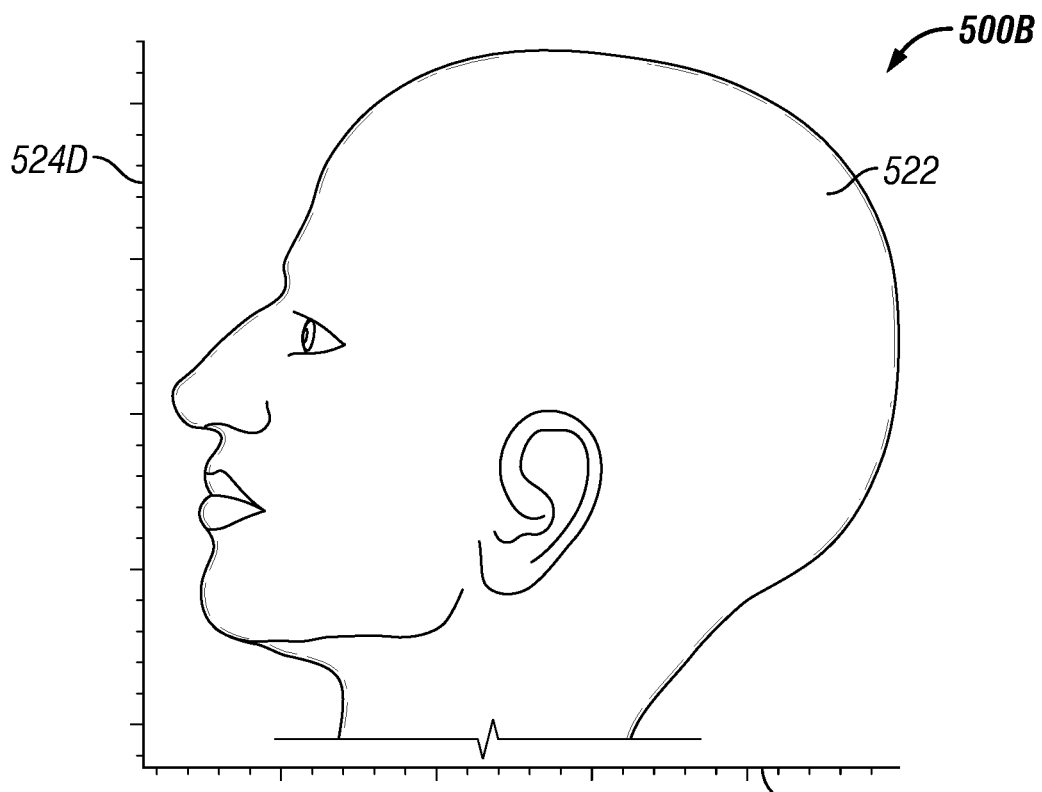
FIG. 5B is a side illustration of a scanned head for a parametric processing.

FIG. 5B is a side illustration of a scanned head 522 for a parametric processing 500B. In at least one version of the parametric processing 500B, at least one axis is provided. The axis(s) 524D, and/or 524E provide a reference for the dimensions of a patient's head as scanned. A parametric model may be developed from the scanned head 522. During the development of the parametric model, a user may rotate or change the viewing angle of the scanned head 522 to allow for different details to be seen or analyzed. With respect to FIGS. 5A and 5B, a process can be utilized to convert an image, set of images, or imaging output for utilization with a processing program that allows for the creation of a personalized scalp cap (not illustrated). For example, the data may be in one format such as, but not limited to, comma separated values (CSV), or an excel format XSL or XSLX, or other data format for specific programs or systems such as a 3D or three-dimensional scanner. If data provided from the scanning is in a format that is unusable then it would be necessary to utilize a program that can convert, or transform the data into a usable format. Any computer, processor, or computing device may be utilized to generate, create, process, and/or develop the parametric model.

Figure 6:
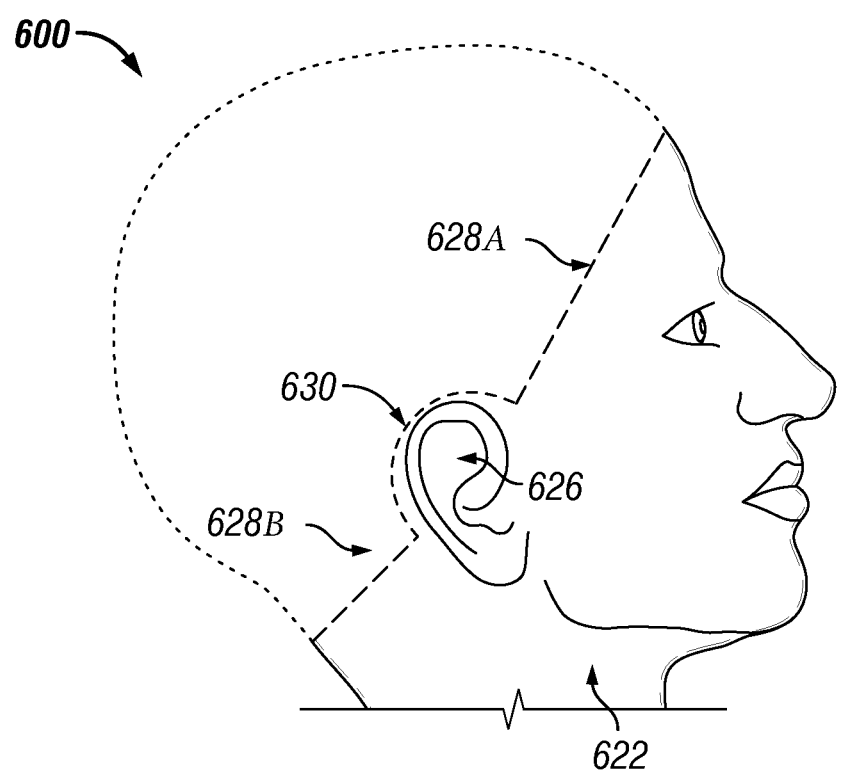
FIG. 6 is a side view illustration of a scanned head, for parametric processing.

FIG. 6 is a side view illustration of a scanned head 622, for parametric processing 600. In at least one version, the parametric processing 600 can include establishing the hair line of a scanned head 622 and can include the nape line 628A and the brow line 628B (collectively 628) of a personalized scalp cap (not illustrated). Some of the additional factors to consider are generating an ear cutout 630 to allow for the scalp cap (not illustrated) to rest tight against and/or behind the ear 626 of a patient. The nape line 628A and the brow line 628B, along with the ear cutout 630 may be calculated and/or generated by a computing device, processor, or program. In some examples, one or more of the nape line 628A, brow line 628B, or ear cutout 630 may be selected manually, and the remainder calculated and/or generated by a computing device, processor, or program. In at least one embodiment, the nape line 628A, brow line 628B, and ear cutout 630 are automatically determined and/or calculated by a computing device, processor, or program based on the data provided during the scanning or parametric processing steps. A graphical user interface (GUI) may be utilized to illustrate the determination and/or calculation performed by a computing device, processor, or program. In the event that the determination and/or calculation is incorrect due to an issue with the data provided to the computing device, processor, or program, or from an unusual scalp or head profile, the GUI, and/or computing device, processor, or program, can allow a doctor or user to select one or more of the nape line 628A, brow line 628B, and/or ear cutout 630 to manually adjust or reset the line(s). If a line has been adjusted and/or reset then all the remaining lines may be determined and/or calculated again by the computing device, processor, or program.

Figure 7:
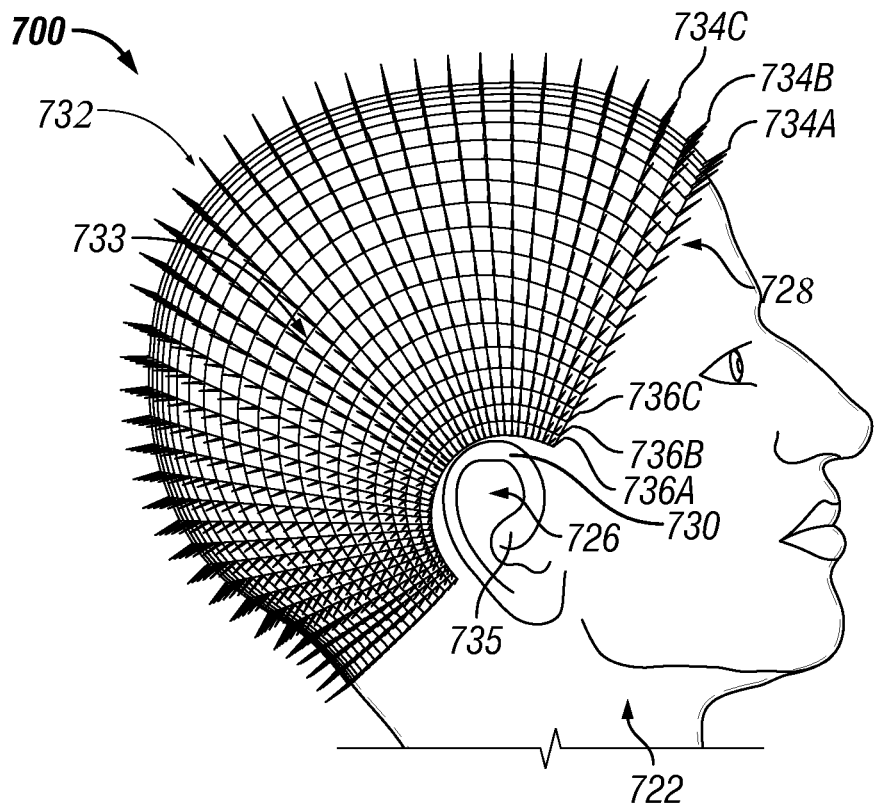
FIG. 7 is a side view illustration of a scanned head, for parametric processing.

FIG. 7 is a side view illustration of a scanned head 722, for parametric processing 700. After the generation of the hair line 728 and the ear cutout 730 around and/or behind the ear 726, a polar grid 732 can be generated. The polar grid 732 allows for longitudinal lines 734A, 734B, 734C (collectively 734) and latitudinal lines 736A, 736B, 736C (collectively 736). The longitudinal lines 734 and the latitudinal lines 736 allow for the conversion to polar coordinates from parametric processing and incorporation of any changes and/or differences of the scanned head 722. Polar coordinates also allow for a parametric model that follows the curvature of a human head. In at least one version, the parametric processing 700 generates a parametric model that sets the longitudinal lines 734 at fixed angles from a centroid point 735, and the latitudinal lines are set at fixed distances 733 from each other starting from a centroid point 735. The centroid point 735, in at least one example can be the center of the ear 726. While in other examples, the centroid point 735 can be offset from the ear 726. In some versions, the longitudinal limes 734, and/or the latitudinal lines 736 may include or be generated from finite element method analysis, and/or a finite element method mesh. In other versions, dimensional analysis can be utilized to generate a parametric model for the scanned head 722.

Figure 8:
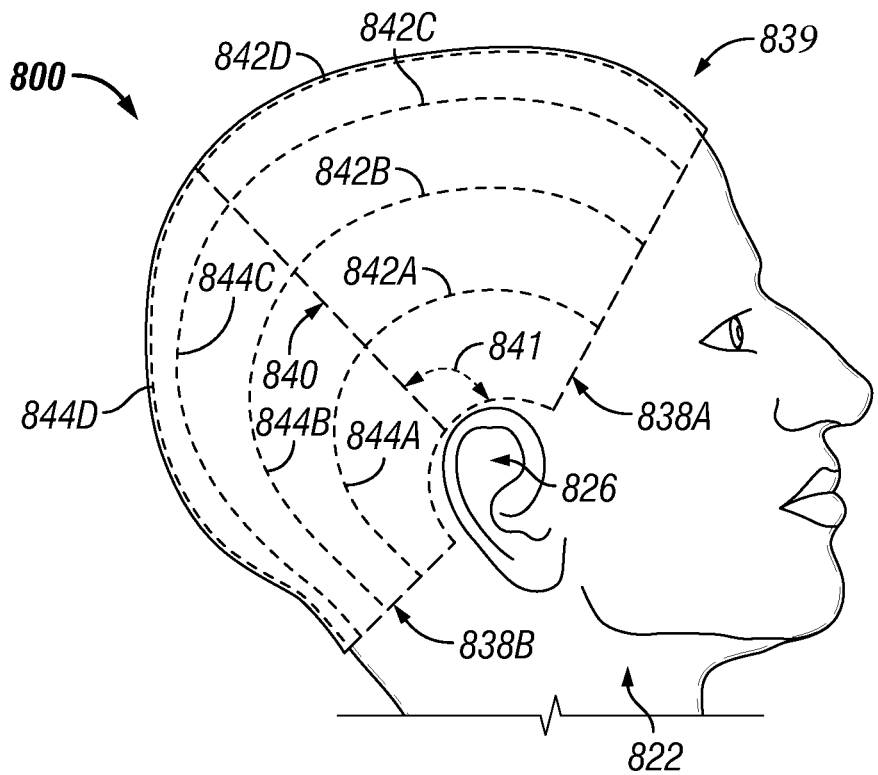
FIG. 8 is an illustration of a scanned head, for parametric processing.

FIG. 8 is an illustration of a scanned head 822, for parametric processing 800. After a parametric model has been generated an overlay 839 can be generated from the parametric model. The overlay 839 can set the brow line 838A, the nape line 838B, and/or the linking line 840 from the ear 826 of a patient or scanned head 822 to the opposite ear (not shown). The interpolated parametric model or modified parametric model can be remapped with an angle variable 841 to a fixed value line or linking line 840, producing an equally spaced set of lines or section(s). The spacing of the lines or sections can be calculated to have the lines spaced with a variation of less than a value provided. The variation value may also be utilized to set the linking line 840, which in at least one version can be set closer to the nape line 838B than the brow line 838A. In at least one example, the overlay can also include forward radial section(s) 842A, 842B, 842C, and/or 842D (collectively 842), and/or rearward radial section(s) 844A, 844B, 844C, and/or 844D (collectively 844). The overlay 839 can also be a remapping of an interpolation of a parametric model. The overlay 839 can then be utilized to generate a design file. The design file could be generated automatically, by a computing device, processor, or program, or it may be semi-automatically generated with some selections made by a doctor or other user. In some examples, the overlay 839 may be calculated and/or generated based on the position of the x-axis, and/or symmetry around the x-axis.

FIG. 9A is an illustration of a design file output 951 from a parametric processing 900A. The design file output 951, in at least one version, may include a linking section 950, a forward central section 952A, a rearward central section 952B, a first set of forward radial section(s) 958A, 958B, 958C, and/or 958D (collectively 958), a second set of forward radial section(s) 960A, 960B, 960C, and/or 960D (collectively 960), a first set of rearward radial section(s) 956A, 956B, and/or 956C (collectively 956), and a second set of radial section(s) 962A, 962B, and/or 962C (collectively 962). The design file output 951 may be generated from the interpolated or modified parametric model. A lower gap angle 949, and/or an upper gap angle 947 may be calculated for the forward radial sections, and the rearward radial sections to allow for the proper divisions and interaction of the individual sections.

The linking section 950 can have a first end 954A and a second end 954B distal from one another. In at least one version, the first end 954A with one side being coupled to the linking section, the radius opposite that side can be set during one of the processing steps to provide the proper radial angles to allow for an ear cutout. The first end 954A can also be coupled to a first forward radial section 958A of the first set of forward radial section(s) 958, and/or a first rearward radial section 956A of the first set of rearward radial section(s) 956. Similarly, the second end 954B with one side being or coupled to the linking section, the radius opposite that side can be set during one of the processing steps to provide the proper radial angles to allow for an ear cutout. The second end 954B can also be coupled to a first forward radial section 960A of the second set of forward radial section(s) 960, and/or a first rearward radial section 962A of the second set of rearward radial section(s) 962.

The first set of forward radial sections 958, the second set of forward radial sections 960, and the forward central section 952A can be coupled to the linking section 950 through thread, fasteners such as, but not limited to hook and loop, glues, adhesives, or other similar or like methods of attachment and/or coupling. Similarly, the first set of rearward radial sections 956, the second sec of rearward radial sections 962, and the rearward central section 952B can be coupled to the linking section 950 through thread, fasteners such as, but not limited to hook and loop, glues, adhesives, or other similar or like methods of attachment and/or coupling.

FIG. 9B is an illustration of a design file output 951 from a parametric processing 900A, placed on the head of a patient 922. The design file output 951 can also be exported to a printer, stamper, 3D printer, fabric, sewing, heat or frequency welding, and/or other methods or processes for manufacturing or creating a scalp cap. The linking section 950 can couple the set of forward radial section(s) 960A, 960B, 960C, and/or 960D (collectively 960), and the set of rearward radial section(s) 962A, 962B, and/or 962C (collectively 962). An end 954B of the linking section 950 allows for the first forward radial section 960D, and the first rearward radial section 962A to properly allow for a cutout around the ear 926 of a patient 922. The radial section(s) 960/962 can mate together, or with the linking section 950, to provide a unique and/or personalized fit for each patient 922. In at least one version, each radial section 960/962, central section(s) 952, and linking section 950 may have a cooling channel that passes through it. The cooling channel(s) may be for each individual section with each section having its own input and output, while in other embodiments there may be one single channel with a portion of the channel dedicated to each section. In at least one example, the fluid would flow from the entrance on a right rear side through channels on the rear right side of the scalp cap, and then through channels on the right side of the scalp cap and then through channels on the top of the scalp cap, and then through channels on the left side of the scalp cap, and then through channels on the left rear of the scalp cap before exiting at the exit on the left hand side of the rear of the scalp cap.

Figure 9C:
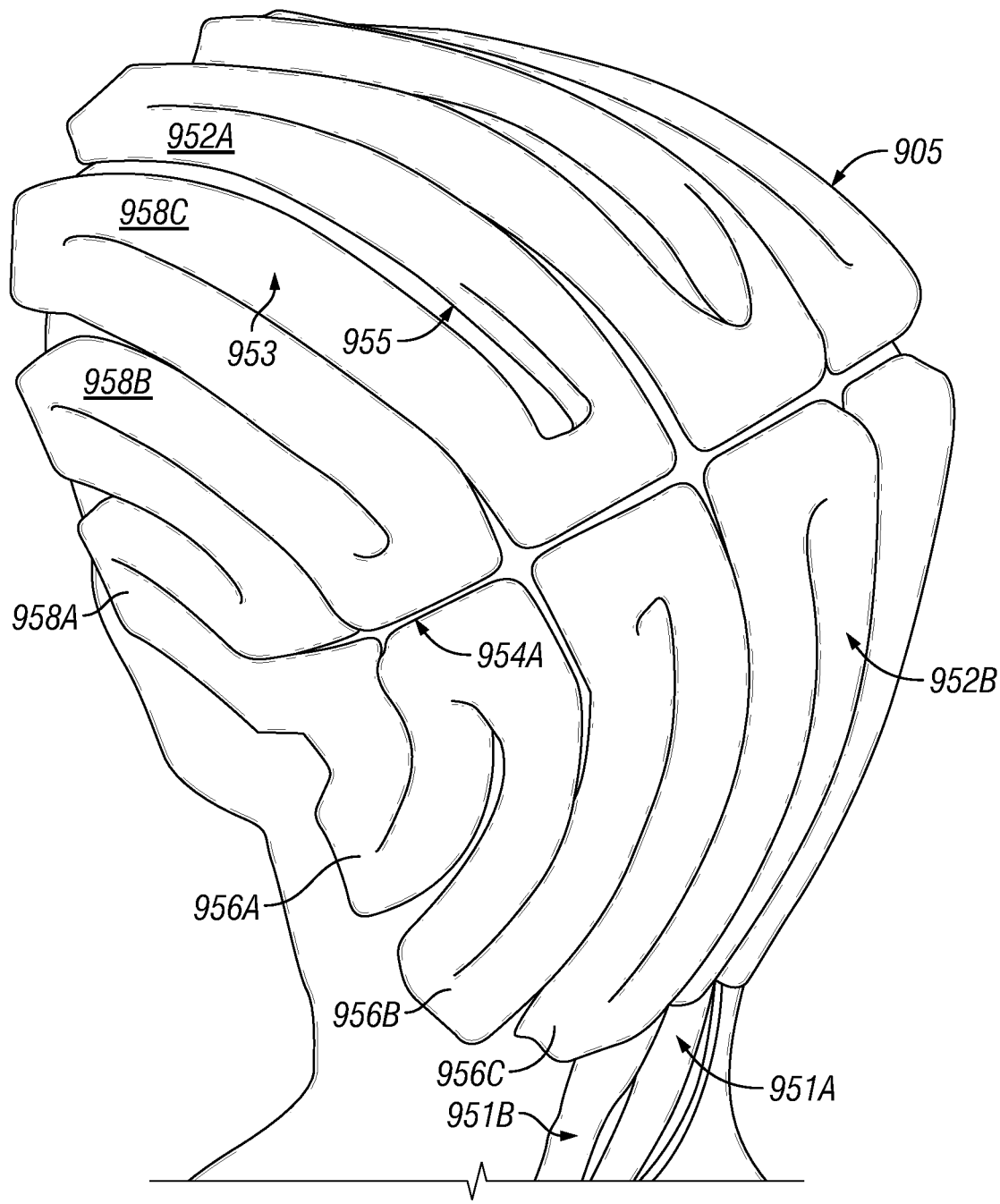
FIG. 9C is an illustration of a scalp cap as generated from the parametric processing.

FIG. 9C is an illustration of a scalp cap 905 as generated from the parametric processing. The scalp cap 905, can have at least one cooling channel (collectively 951) illustrated as a cooling channel input 951A, and a cooling channel output 951B. The cooling channel(s) 951 allow for a cooling fluid 953 to be flowed and/or pumped through the scalp cap 905. The rearward radial section(s) 956A, 956B, and/or 956C (collectively 956), forward radial section(s) 958A, 958B, and/or 958C (collectively 958), forward central section 952A, and rearward central section 952B can each have their own individual cooling channels that can intersect and/or couple to the previous section or be fluidly coupled to the cooling channel input and/or output 951. The section(s) 952, 956, and/or 958 may each individually be separated by a cut or separation channel 955 that allows each individual section to increase in closeness to the scalp. The cut or separation channel 955 can be the points or sections along the scalp cap 905, where the section(s) are separated, include but not limited to, a separation such as that illustrated by the upper gap angle 947 of FIG. 9A. A central linking channel 950 can allow the forward and rearward section(s) to be separately aligned and conforming to the patient's scalp and/or head. The scalp cap 905 allows for a temperature difference between the scalp and the scalp cap 905 to be less than sixteen (16) degrees centigrade. Ideally, a temperature difference of zero degrees is the best result. The fluid pumped through the scalp cap 905, would generally have a temperature range of 0-5 degrees Centigrade. The pressure of the fluid in at least one embodiment would be approximately 0.20 bars or lower, and the rate of flow can be 1.5 liters per minute or less.

Figure 10:
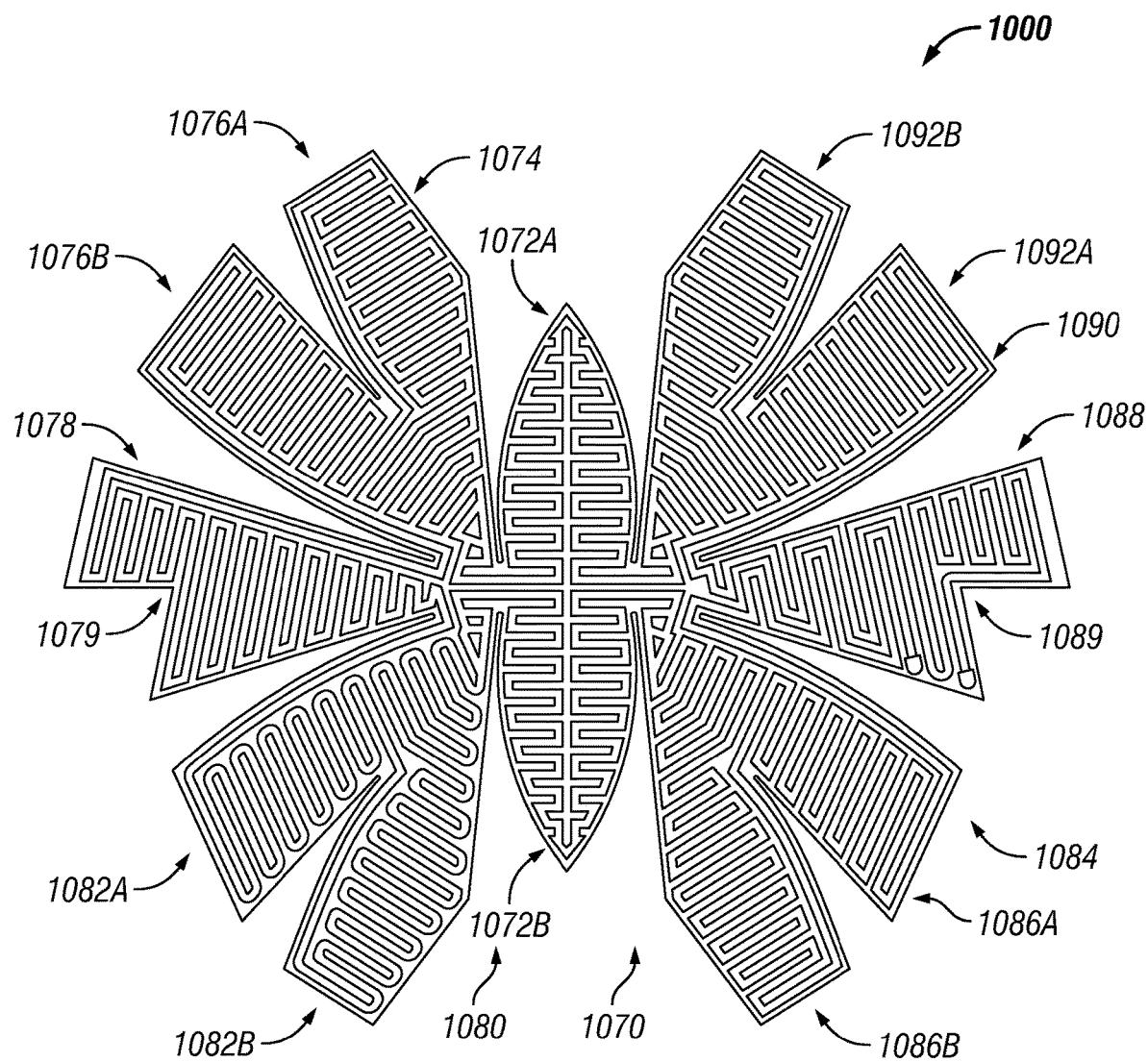
FIG. 10 is an illustration of an alternative design output from a parametric process.

FIG. 10 is an illustration of an alternative design output 1070 from a parametric process 1000. The design output 1070 can include a forward central section 1072A, and a rearward central section 1072B. The central sections 1072, in at least one example are pointed or arrowhead shaped to allow for the angling of the remaining sections to provide a proper fit. The first forward petal 1074 can have two offshoots 1076A and 1076B. Similarly, the second forward petal 1090 can have a first offshoot 1092A and second offshoot 1092B. The rear section petals 1080 and 1084 each have two offshoots 1082A, 1082B, and 1086A, 1086B. The side petals 1078 and 1088 each have a notch 1079/1089 to allow for the design output 1070 to conform around a patient's ear.

Figure 11:
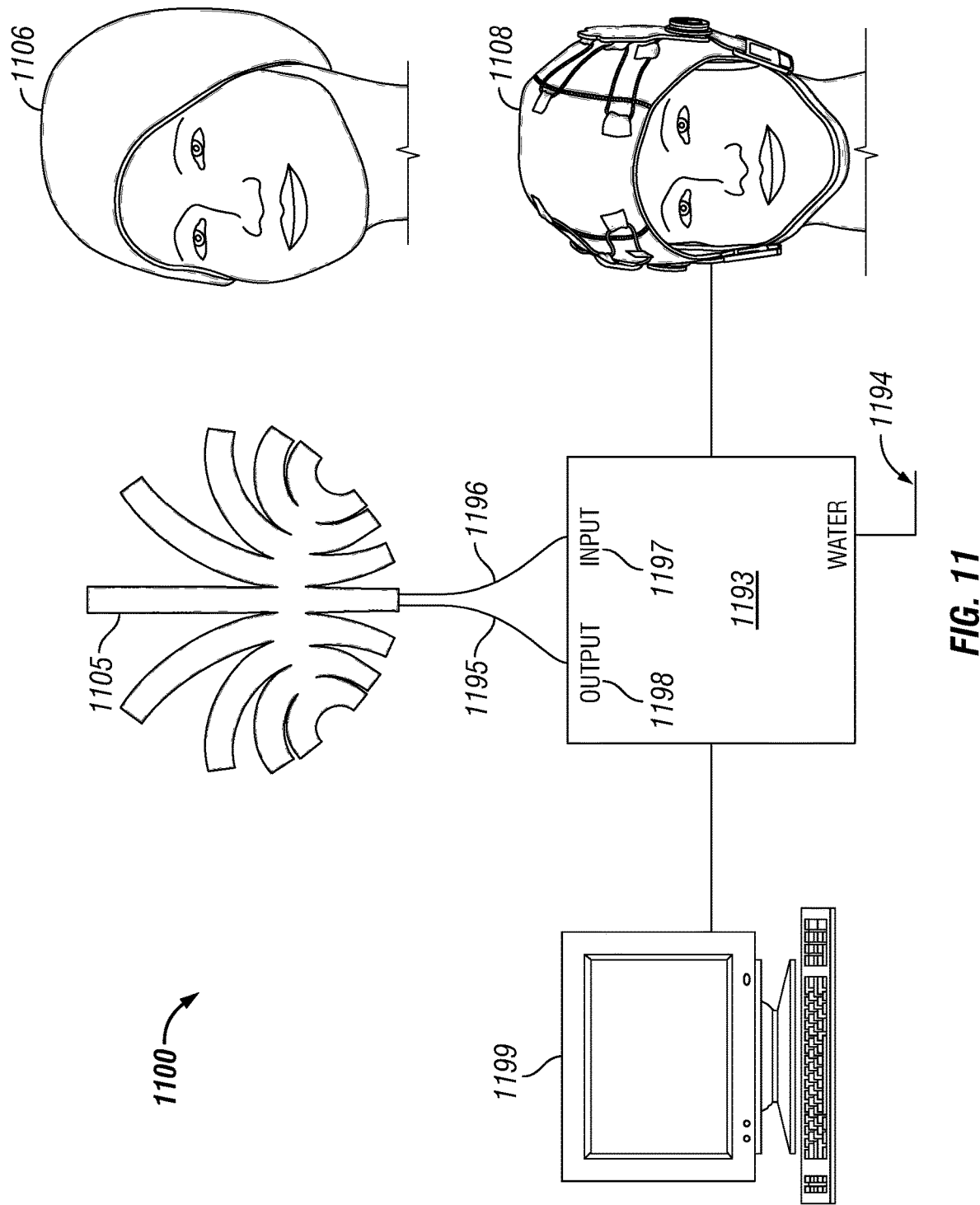
FIG. 11 is an illustration of a cooling system.

FIG. 11 is an illustration of a cooling system 1100. The cooling system 1100 can include a scalp cap 1105, a thermal cap 1106, a securing cap 1108, a cooling channel 1195/1196, and a cooling device 1193 that may have an input 1197 and/or an output 1198. The cooling device 1193, may be coupled to a computing device configured to generate control signals, and/or evaluate or analyze the effects of the cooling system 1100. In at least one version, a patient or the provider (not illustrated) can place each of the cap(s) 1105, 1106, and/or 1108 onto the head allowing a cooling channel 1165/1166 to be coupled from the scalp cap 1105 to the cooling device 1193. A cooling fluid can traverse the cooling channel 1195/1196, and/or channels throughout the scalp cap 1105 to provide a cooling effect to the scalp and/or hairline of a patient (not illustrated). The cooling fluid can include water, and other fluid 1194 capable of transferring a temperature difference. A cooling fluid may be passed from the cooling device that operates to cool the temperature of the fluid, while maintaining the fluid above 0 degrees Centigrade or freezing. The cooling device can operate with an alcohol based fluid, that can be pumped by at least one fluid pump. The fluid pump may also be coupled to sensors, such as temperature sensors, that can trigger operational changes of the pump or the fluid cooling mechanisms of the cooling device. The cooling device in at least one embodiment may be a C3 Dignicap.

The present disclosure may also include a computing device that can include any of an application specific integrated circuit (ASIC), a microprocessor, a microcontroller, a digital signal processor (DSP), a field-programmable gate array (FPGA), or equivalent discrete or integrated logic circuitry. In some examples, the system may include multiple components, such as any combination of one or more microprocessors, one or more microcontrollers, one or more DSPs, one or more ASICs, or one or more FPGAs. It would also be understood that multiples of the circuits, processors, or controllers could be used in combination or in tandem, or multithreading.

The components of the present disclosure may include any discrete and/or integrated electronic circuit components that implement analog and/or digital circuits capable of producing the functions attributed to the modules herein. For example, the components may include analog circuits, e.g., amplification circuits, filtering circuits, and/or other signal conditioning circuits. The components may also include digital circuits, e.g., combinational, or sequential logic circuits, memory devices, etc. Furthermore, the modules may include memory that may include computer-readable instructions that, when executed cause the modules to perform various functions attributed to the modules herein.

Memory may include any volatile, non-volatile, magnetic, or electrical media, such as a random-access memory (RAM), dynamic random access memory (DRAM), static random access memory (SRAM), read-only memory (ROM), non-volatile RAM (NVRAM), electrically-erasable programmable ROM (EEPROM), flash memory, hard disks, or any other digital media. Additionally, there may also be a tangible non-transitory computer readable medium that contains machine instructions, such as, a (portable or internally installed) hard drive disc, a flash drive, a compact disc, a DVD, a zip drive, a floppy disc, optical medium, magnetic medium, or any other number of possible drives or discs, that are executed by the internal logic of a computing device. It would be understood that the tangible non-transitory computer readable medium could also be considered a form of memory or storage media.

Figure 12:
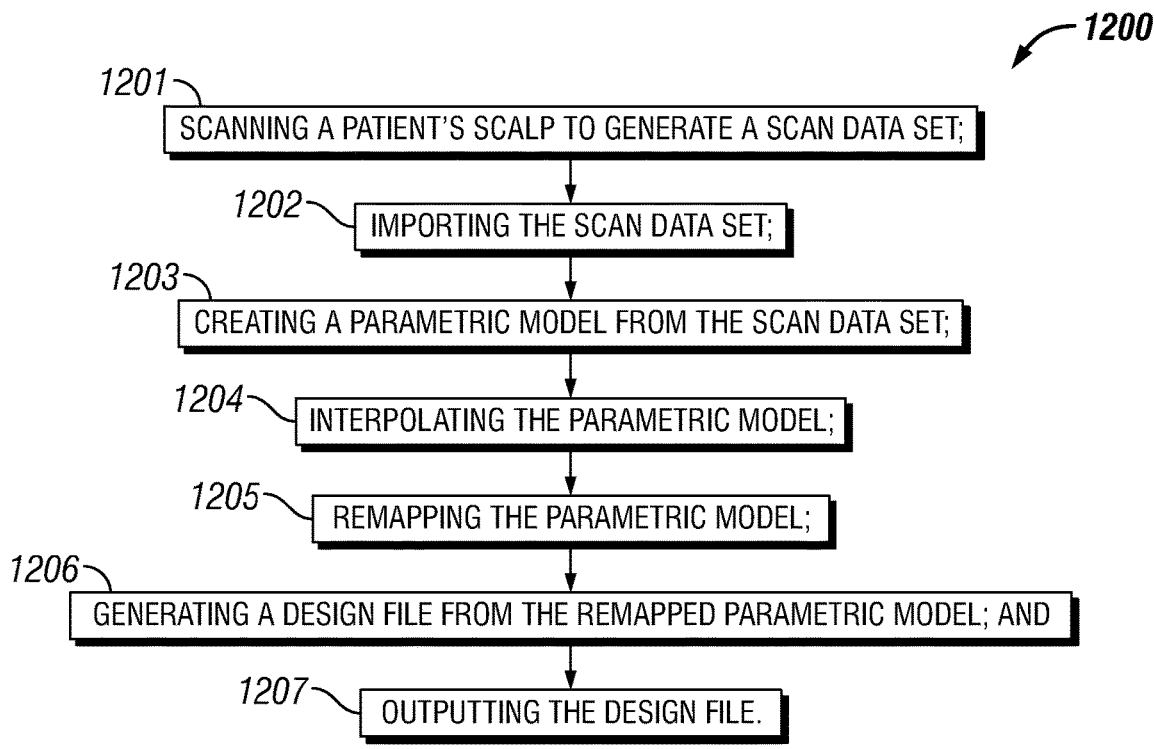
FIG. 12 is an illustration of a method of manufacture for a scalp covering.

FIG. 12 is an illustration of a method of manufacture for a scalp covering 1200. A scalp cap or covering (not illustrated) can be prepared from a scanning procedure that includes the use of systems or devices such as, but not limited to, 3D scanning, X-Ray, CAT scan, MIR, or other imaging systems or devices for scanning a patient's scalp to generate a scan data set 1201. The data acquired from the scanning can be utilized as a scan data set by a program (or a program executed from a computer related medium), processor, or computing device. In at least one version, the scan data set can be imported by a computing device, processor, or program 1202. The importing step can also include the conversion of the scan data set from a first file format, to a second file format. In some examples, a rendering of the scan data set may be performed during the importation step. The rendering may include at least one axis to provide a contextual or dimensional reference for the rendered data.

The creating a parametric model from the scan data set step 1203, in at least one version, includes determining criteria for each individual patient, the centroid point on a patient's head, the minimum azimuthal angle along the nape of a patient, the maximum azimuthal angle at the forehead of a patient, and the radius in angle around the ear of the patient. In some examples, one of the criteria is selected manually allowing the remaining necessary criteria to be calculated, while in other examples all the criteria can be calculated by a computing device, processor, or program. A parametric model can then be created from the determined or calculated criteria, and the scan data set.

The parametric model can then be interpolated 1204. The interpolating the parametric model step can also include interpolating the radial dimensions of a patient's head, interpolating at least one surface point of a patient's head, interpolating the normal vector of a patient's head, interpolating a cross-line distance for a specific set of points on a patient's head, interpolating a distance forward from the nape along a constant angle from a specified set of points on a patient's head, interpolating an azimuthal angle halfway between the nape and forehead of a patient. These interpolations and calculation can be stored as part of the parametric model, or a modified parametric model.

A remapping of the parametric or modified parametric model 1205 can allow for the parametric model or modified parametric model to be divided into a forward section, a rearward section, and a linking section. The remapping allows for angles calculated and/or generated as part of the parametric or modified parametric model may be utilized to generate fixed angles, and/or fixed lines or distances. The fixed angles, and/or fixed lines or distances can then be utilized to divide specific portions of the scanned head of a patient into fixed sections. The sections can have any number of shapes and/or sizes, based on the dimensions of the scanned head of a patient. The shapes and/or sizes can be based on ratios, minimum, and/or maximum dimensions that allow the remapped parametric model to be within certain design specifications, that may be preprogramed or specified during the remapping step to reduce the variation.

The remapped parametric file can then be utilized to generate a design file 1206. The design file can be generated to reduce the number of forward and rearward sections. The number of sections can be based on a variation value, and/or the azimuthal angle(s) of the individual sections. In at least one version, the linking section that couples the forward and rearward sections can be generated at a position close to the nape line than the brow line. In other versions, the linking section position may be generated based on a symmetry above and/or below the x-axis of the scanned patient head. The sections may also include a forward and/or rearward gap(s) that can be on the number of individual section(s) and/or the angles utilized in the design file.

The design file may also include a polyhedral segmented surface created from a function utilizing a forward or reward flag, the individual section flag, the individual section angle flag, and/or the position flag. In at least one version, the flags could also include a set of values. The design file can then be output as a data file or be sent directly to a manufacturing system or device. The design data file could output 1207 in any number of data formats, including but not limited to, JPG, PNG, TIFF, STL, CAD, CSV, XLSX, or other similar data formats.

Figure 13:
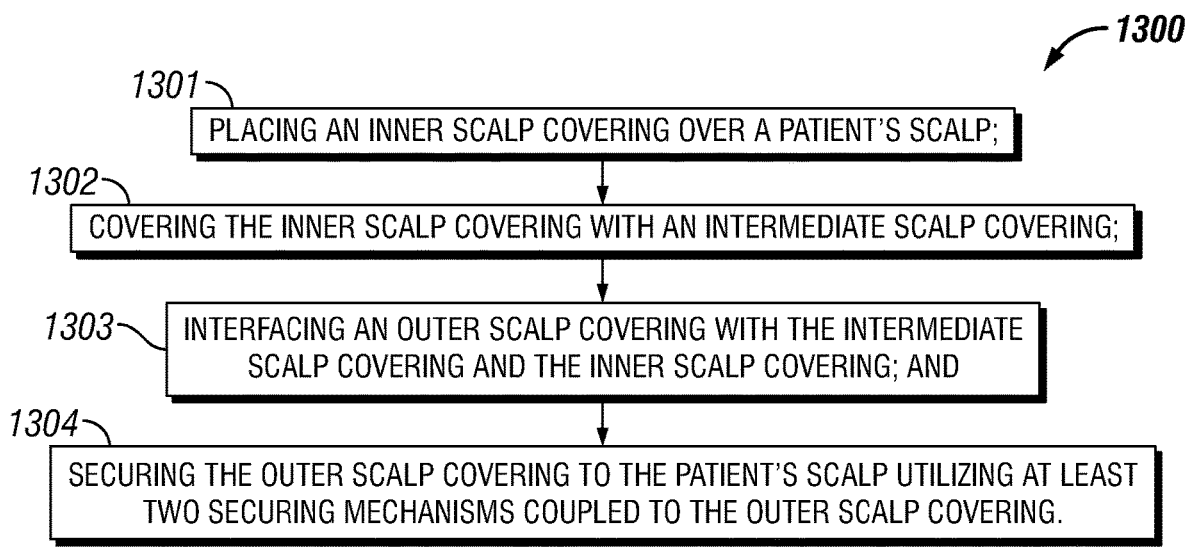
FIG. 13 is an illustration of a method of use for a scalp covering system.

FIG. 13 is an illustration of a method of use for a scalp covering system 1300. A patient may place an inner scalp covering over their scalp 1301. The inner scalp covering may also be fluidly coupled to a cooling device or system through a cooling channel. The inner scalp covering device may then be covered with an intermediate scalp covering 1302. The intermediate scalp covering can also include thermally resistive materials to assist in maintaining a cooling effect along the scalp of a patient. An outer scalp covering can be interfaced with the intermediate scalp covering and the inner scalp cover 1303. The outer scalp covering can have at least one securing mechanism. A securing of the outer scalp covering to the patient's scalp can occur by utilizing at least two securing mechanisms coupled to the outer scalp covering 1304. A patient may also wet their hair to provide a better fit and/or cooling effect for the cooling device and/or system.

While this disclosure has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While various embodiments in accordance with the principles disclosed herein have been described above, they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

We claim:

1. An apparatus for a scalp covering comprising:
   a linking section having a first end and a second end;
   a forward central section coupled to the linking section at a first forward central section end;
   a rearward central section coupled to the linking section at a first rearward central section end;
   a set of forward left radial sections coupled to the linking section wherein the set of forward left radial sections comprises at least two forward left radial sections that are each progressively further in distance from the forward central section wherein each of the at least two forward left radial sections are movable with respect to an adjacent forward left radial section;
   a set of forward right radial sections coupled to the linking section wherein the set of forward right radial sections comprises at least two forward right radial sections that are each progressively further in distance from the forward central section wherein each of the at least two forward right radial sections are movable with respect to an adjacent forward right radial section;
   a set of rearward left radial sections coupled to the linking section wherein the set of rearward left radial sections comprises at least two rearward left radial sections that are each progressively further in distance from the rearward central section wherein each of the at least two rearward left radial sections are movable with respect to an adjacent rearward left radial section; and
   a set of rearward right radial sections coupled to the linking section wherein the set of rearward right radial sections comprises at least two rearward right radial sections that are each progressively further in distance from the rearward central section wherein each of the at least two rearward right radial sections are movable with respect to an adjacent rearward right radial section.

2. The apparatus of claim 1, wherein the linking section is manufactured of a thermally conductive material.

3. The apparatus of claim 1, wherein the forward central section or the rearward central section is manufactured of a thermally conductive material.

4. The apparatus of claim 1, wherein the radial sections are manufactured of a thermally conductive material.

5. The apparatus of claim 1, further comprising a first set of tubular members for circulation of a cooling fluid through the scalp covering.

6. The apparatus of claim 5, wherein a plurality of the sections each comprise a portion of the first set of tubular members.

7. The apparatus of claim 6, wherein the portion of the first set of tubular members extends from the linking section along a length of one of the plurality of sections and back to the linking section.

8. The apparatus of claim 5, wherein the first set of tubular members are fluidly connected to a cooling device.

9. The apparatus of claim 1, wherein each of the forward left radial sections and the forward right radial sections are coupled perpendicularly to the linking section and substantially parallel to the forward central section.

10. The apparatus of claim 1, wherein each of the rearward left radial sections and the rearward right radial sections are coupled perpendicularly to the linking section and substantially parallel to the rearward central section.

11. A system for scalp covering comprising:
    an inner scalp covering, wherein the inner scalp covering further comprises a linking section having a first end and a second end,
       a forward central section coupled to the linking section at a first forward central section end,
       a rearward central section coupled to the linking section at a first rearward central section end,
       a set of forward left radial sections coupled to the linking section wherein the set of forward left radial sections comprises at least two forward left radial sections that are each progressively further in distance from the forward central section wherein each of the at least two forward left radial sections are movable with respect to an adjacent forward left radial section;
       a set of forward right radial sections coupled to the linking section wherein the set of forward right radial sections comprises at least two forward right radial sections that are each progressively further in distance from the forward central section wherein each of the at least two forward right radial sections are movable with respect to an adjacent forward right radial section;

a set of rearward left radial sections coupled to the linking section wherein the set of rearward left radial sections comprises at least two rearward left radial sections that are each progressively further in distance from the rearward central section wherein each of the at least two rearward left radial sections are movable with respect to an adjacent rearward left radial section; and a set of rearward right radial sections coupled to the linking section wherein the set of rearward right radial sections comprises at least two rearward right radial sections that are each progressively further in distance from the rearward central section wherein each of the at least two rearward right radial sections are movable with respect to an adjacent rearward right radial section;

an intermediate scalp covering; and an outer scalp covering.

12. The system of claim 11, wherein the inner scalp covering is constructed of a thermally conductive material.

13. The system of claim 11, wherein the intermediate scalp covering is constructed of a thermally non-conductive material.

14. The system of claim 11, wherein the outer scalp covering is constructed of a thermally resistant material.

15. The system of claim 11, wherein the inner scalp covering is fluidly coupled to a cooling device.

16. The system of claim 11, wherein the outer scalp covering further comprises a first securing mechanism, and a second securing mechanism.

17. The system of claim 16, wherein the outer scalp covering is secured against a patient's scalp via the first securing mechanism and the second securing mechanism.

18. The system of claim 17, wherein the outer scalp covering can be dynamically adjusted using the first and second securing mechanisms to press the inner scalp covering to a patent's scalp.

19. The system of claim 11, wherein the inner scalp covering is further comprises a plurality of the sections each comprise a portion of a first set of tubular members.

20. The system of claim 19, wherein the tubular members are coupled fluidly to a cooling device.

* * * * *